United States Patent [19]

Hudlicky et al.

[11] Patent Number: 5,600,014
[45] Date of Patent: Feb. 4, 1997

[54] SYNTHESES OF D-CHIRO-3-INOSOSE AND (+)-D-CHIRO INOSITOL

[75] Inventors: Tomas Hudlicky; Martin Mandel, both of Blacksburg, Va.

[73] Assignee: Virginia Tech Intellectual Properties, Inc., Blacksburg, Va.

[21] Appl. No.: 410,477

[22] Filed: Mar. 24, 1995

Related U.S. Application Data

[60] Division of Ser. No. 974,057, Nov. 10, 1992, abandoned, which is a continuation-in-part of Ser. No. 956,522, Oct. 5, 1992, abandoned.

[51] Int. Cl.$^6$ ....................................................... C07C 45/42
[52] U.S. Cl. ................................................ 568/361; 568/363
[58] Field of Search ....................................... 568/361, 363

[56] References Cited

U.S. PATENT DOCUMENTS 5,091,596  2/1992  Kennington et al. .
5,200,516  4/1993  Hudlicky .

FOREIGN PATENT DOCUMENTS

WO91/16290  10/1991  WIPO .

OTHER PUBLICATIONS

H. Z. Sable et al. (1963) Helevtica Chimica Acta, vol. 46, Fasciculus IV, No. 129–130, pp. 1157–1165.

Hudlicky, T.; Price J. D.; Tsunoda, T. —"Efficient and Enantiodivergent Synthesis of (+)– and (–)–Pinitol"; J. Am. Chem. Soc. 1990, 112, 9439–9440.

Rudloff, E. von —"Permanganate Oxidation of Occidentalol: Unexpected Epoxide Formation"; Tetrahedron Letters No. 10, pp. 993–998, 1966, Pergamon Press Ltd., U.K.

Ganey, M. V.; Padykula, R. E.; Berchtold, G. A.; —"Resolution of trans–1,2–Dihydroxy–1,2–dihydrobenzene for the Preparation of Optically Pure Benzene Diol Epoxides. Preparation of Bromo– and Chlorobenzene Diol Epoxides"; J. Org. Chem. 1989, 54, 2787–2793.

Carless, H., Tetrahedron Letters, vol. 33, No. 42, pp. 6397–6382 (1992).

Mandel, M. and Hudlicky, T., The Journal of Organic Chemistry, vol. 58, No. 8, pp. 2331–1333 (1993).

Mandel, M. and Hudlicky, T., J. Chem. Soc. Perkin Trans.1, pp. 741–743 (1993).

*Primary Examiner*—Nicky Chan
*Attorney, Agent, or Firm*—Kirsten A. Anderson

[57] ABSTRACT

There are described novel biocatalytic and chemical processes for the synthesis of various oxygenated compounds. Particularly, there are described processes for the synthesis of a useful synthon 12 made by reacting a protected diol (acetonide) with permaganate under appropriate conditions. Such synthon is useful of the synthesis of various pharmaceutically important compounds such as D-chiro-inositol and D-chiro-3-inosose. Also, there are disclosed novel compounds, including specifically the synthon 12 and compounds derived therefrom.

5 Claims, No Drawings

SYNTHESES OF D-CHIRO-3-INOSOSE AND (+)-D-CHIRO INOSITOL

This is a division of application Ser. No. 07/974,057 filed Nov. 10, 1992, now abandoned which is a continuation in part of U.S. application Ser. No. 07/956,522, filed Oct. 5, 1992 (now abandoned).

FIELD OF THE INVENTION

This invention relates to biocatalytic methods for the synthesis of various oxygenated compounds, such methods comprising enantiomerically selective functionalization of arene cis-diol starting materials to potentially all of the nine known inositols, shown below. More particularly this invention relates to the synthesis of specific compounds including but not limited to D-chiro-3-inosose 10, and D-chiro-inositol 6, shown below, and also relates to the necessary methods of synthesis for at least three other inositols, neo-, muco-, and allo-inositols.

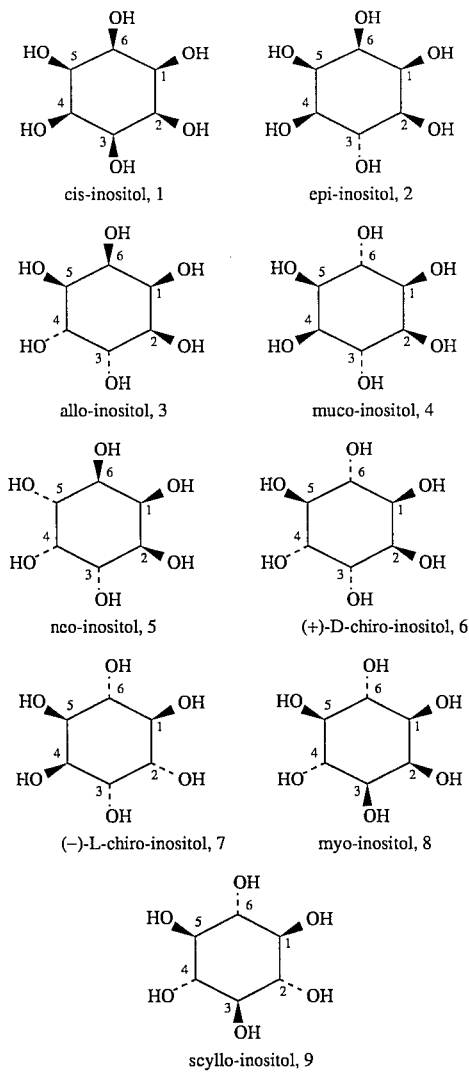

(+)-D-chiro-inositol 6 is of particular interest due to its perceived potential as an antidiabetic agent (See for example: Kennington, A. S.; Hill, C. R.; Craig, J. Bogardus, C.; Raz, I.; Ortmeyer, H. K.; Hansen, B.C.; Romero, G.; Larner, J. *New England J. Med.* 1990, 323, 373).

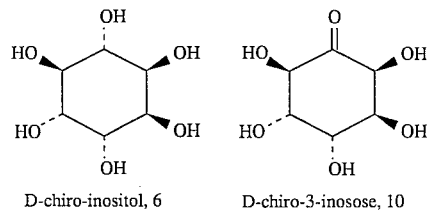

D-chiro-inositol, 6    D-chiro-3-inosose, 10

BACKGROUND OF THE INVENTION

The expression of arene cis-diols was originally discovered and described by Gibson twenty-three years ago (Gibson, D. T. et al. *Biochemistry* 1970, 9, 1626). Since that time, use of such arene cis-diols in enantiocontrolled synthesis of oxygenated compounds has gained increasing acceptance by those skilled in the art. Many examples of applications to total synthesis of carbohydrates, cyclitols, and oxygenated alkaloids can be found in the literature, however much of the work done within this area has been with the more traditional approach of attaining optically pure compounds from the carbohydrate chiral pool. (Hanessian, S. in *Total Synthesis of Natural Products: The Chiron Approach*, 1983, Pergamon Press (Oxford)). Furthermore, none of the work done with these arene cis-diols teaches or suggests the synthesis of the oxygenated compounds which are the subject of the present invention.

In the present invention, unlike in the previous attempts to utilize these arene cis-diols, emphasis has been placed on the application of precise symmetry-based planning to further functionalization of arene cis-diols in enantiodivergent fashion. This approach has previously been successfully applied for the synthesis of cyclitols and sugars. See for example, commonly owned patent applications PCT/US91/02594 (WO 91/16290) and PCT/US91/01040 (WO 91/112257), the disclosure of which is incorporated herein by reference.

Compounds which can be made by the processes set forth herein include oxygenated compounds, however the present processes are particularly useful for the synthesis of compounds such as D-chiro-inositol 6. This compound is potentially an important pharmaceutical agent for the treatment of diabetes. (See for example: a) Kennington, A. S.; Hill, C. R.; Craig, J.; Bogardus, C.; Raz, I.; Ortmeyer, H. K.; Hansen, B.C.; Romero, G.; Larner, J. *New England J. Med.* 1990, 323, 373; b) Huang, L. C.; Zhang, L.; Larner, J. *FASEB*, 1992, A1629, Abstr. #4009; c) Pak, Y.; Huang, L. C.; Larner, J. *FASEB*, 1992, A1629, Abstr. #4008; Larner, Huang, L. C.; Schwartz, C. F. W.; Oswald, A. S.; Shen, T.-Y.; Kinter, M.; Tang, G.; Zeller, K. *Biochem. and Biophys. Commun.* 1988, 151, 1416.).

While the therapeutic potential of D-chiro-inositol 6 is immense, its availability is limited. It is currently available from various sources which are not economically feasible for bulk supply of the drug to the pharmaceutical industry. For example, D-chiro-inositol 6 can be obtained as the demethylation product from (+)-Pinitol. (+)-Pinitol can be made from chlorobenzene via a six step synthetic process as previously described in commonly owned application PCT/US91/02594 incorporated herein. In addition (+)-Pinitol can be obtained by the extraction of wood dust. (Anderson, A. B. *Ind. and Eng. Chem.* 1953, 593). The compound 6 may also be obtained by either cleavage of the natural antibiotic kasugamycin (Umezawa, H.; Okami, Y.; Hashimoto, T.; Suhara, Y.; Hamada, M. Takeuchi, T. *J. Antibiotics* (Tokyo)1965, Ser. A, 18, 101), or by a possible enzymatic inversion of C-3 of the readily available myo-inositol 8. (Umezawa, H.; Okami, Y.; Hashimoto, T.; Suhara, Y.; Hamada, M. Takeuchi, T. *J. Antibiotics* (Tokyo) 1965, Ser. A, 18, 101.7. Umezawa, H.; Okami, Y.; Hashimoto, T.; Suhara, Y.; Hamada, M. Takeuchi, T. *J. Antibiotics* (Tokyo) 1965, Ser. A, 18, 101).

While these methods for synthesis of D-chiro-inositol 6 have been described they are not optimal for either clinical or bulk supply of the drug candidate.

Specifically, the known methods of synthesis are not amenable to scaleup or are too lengthy. One of the methods involves extraction of pinitol from wood dust (Anderson, A. B. *Ind. and Eng. Chem.* 1953, 593) and its chemical conversion to D-chiro-inositol. This procedure, applied to ton-scale would use large volumes of solvents and large quantities of other chemicals and would be either impractical or costly or both. The preparation of D-chiro-inositol from the antibiotic kasugamycin (Umezawa, H.; Okami, Y.; Hashimoto, T.; Suhara, Y.; Hamada, M. Takeuchi, T. *J. Antibiotics* (Tokyo) 1965, Ser. A, 18, 101) also suffers from drawbacks because, on a large scale, about half of the acquired mass of product would be committed to waste (the undesired amino sugar portion of kasugamycin), not to mention the expense with the development of the large scale fermentation process for this antibiotic. The inversion of one center in the available and inexpensive myo-inositol can in principle be accomplished enzymatically (Umezawa, H.; Okami, Y.; Hashimoto, T.; Suhara, Y.; Hamada, M. Takeuchi, T. *J. Antibiotics* (Tokyo) 1965, Ser. A, 18, 101.7. Umezawa, H.; Okami, Y.; Hashimoto, T.; Suhara, Y.; Hamada, M. Takeuchi, T. *J. Antibiotics* (Tokyo) 1965, Ser. A, 18, 101), however no further details on the commercial feasibility of this process have surfaced since 1965.

Based on the shortcomings of the above processes, there is a need for a biocatalytic approach to compound 6 that is an improvement over the above described processes. Such an approach should be environmentally benign as well as amenable to multi-kilogram scale. The currently disclosed process shown in Scheme 1, below is exceedingly brief and efficient in that it provides the epoxydiol 12 in one pot procedure without the necessity of isolation of protected derivative 11. This is an extremely advantageous transformation because it creates four chiral centers in a medium containing water, acetone, magnesium sulfate and manganese dioxide (a naturally occurring mineral), thus making this transformation more efficient and environmentally sound from the point of waste removal.

Scheme 1
Synthesis of D-chiro-Inositol and chiro-3-Inosose

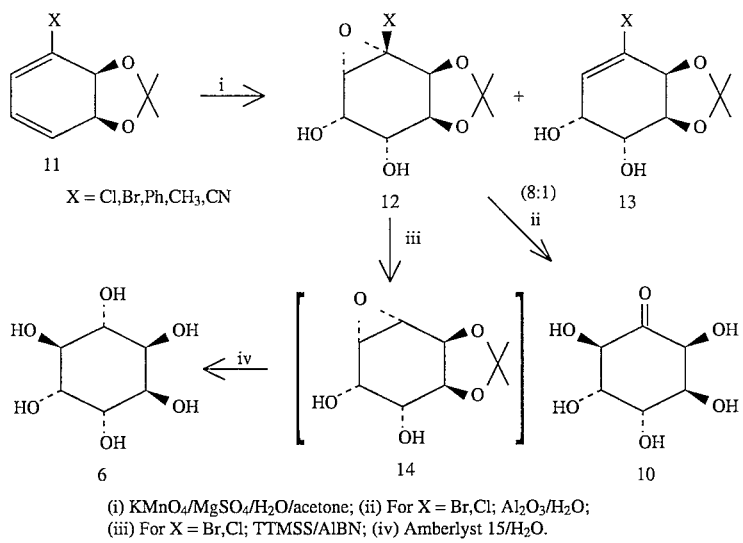

(i) $KMnO_4/MgSO_4/H_2O$/acetone; (ii) For X = Br,Cl; $Al_2O_3/H_2O$;
(iii) For X = Br,Cl; TTMSS/AlBN; (iv) Amberlyst 15/$H_2O$.

Methods for the synthesis of an epoxydiol 14, which is useful as a synthon, have previously been described (Hudlicky, T.; Price, J. D; Rulin F.; Tsunoda, T. *J. Am. Chem. Soc* 1990, 112, 9439) This synthon, which was previously used in the preparation of pinitols, as shown in Scheme 2 below, is now prepared by the controlled oxidation of 11 with potassium permanganate ($KMnO_4$) and a subsequent dehalogenation to 14 rather than previous methods described by Hudlicky et al., and is useful in the synthesis of various other compounds as shown in Scheme 1.

Scheme 2
Enantiodivergent Synthesis of Pinitols

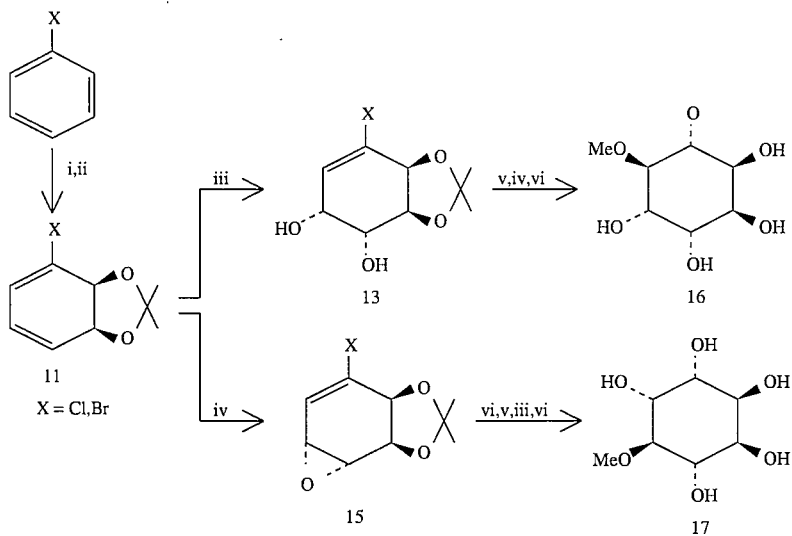

(i) Pp39D; (ii) DMP/H⁺; (iii) OsO₄; (iv) m-CPBA;
(v) LiAlH₄ or Bu₃SnH/AIBN; (vi) MeOH/H⁺.

SUMMARY OF THE INVENTION

Following the biocatalytic production of arene cis-diols, there are described chemical processes for the synthesis of various oxygenated compounds such as those represented by compounds 6,10–28 herein. Further, there are described methods for the synthesis of a substituted epoxydiol 12 useful as a synthon. This synthon 12, prepared by the controlled oxidation of 11 with potassium permanganate (KMnO₄) is useful in the synthesis of various other compounds. The synthesis of the unusual epoxydiol 12 is accomplished as illustrated in Scheme 1.

There are described, chemical processes for the synthesis of various oxygenated compounds such as those represented in Scheme 3 below. Specifically, there are described processes for the preparation of an epoxydiol or an acceptable salt thereof having the formula:

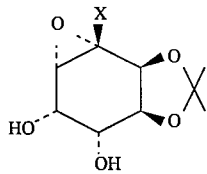

12 wherein X is defined as hydrogen, halogen, alkyl of 1–5 carbon atoms, aryl or CN; the process comprising:
reacting an acetonide of the formula:

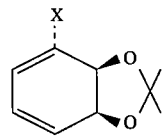

11 wherein X is as defined above; with permanganate in an appropriate solvent at a temperature from about −78° C. to about 40° C. and at a pH of from about 4–8. Preferably, X is Cl, Br, methyl, phenyl or CN.

There is also described a process for the preparation of D-chiro-inositol 6 or a pharmaceutically acceptable salt thereof, comprising reducing the epoxydiol 12 (X═Cl, Br) with a reducing agent to yield compound 14 and then hydrolyzing epoxydiol 14 with a hydrolyzing agent including but not limited to water, an alkaline catalyst, an acidic catalyst, Al₂O₃ or a basic or acidic ion exchange resin.

Also described is a process for the direct hydrolysis of the epoxydiol 12 (X═Cl, Br) to the rare D-chiro-3-inosose 10 and its further reduction to D-chiro-inositol 6, the process comprising hydrolysis of the epoxydiol 12 with a hydrolyzing agent, including but not limited to water, alkaline catalyst, acidic catalyst, basic or acidic ion exchange resin, and then reduction of inosose 10 with a reducing agent.

Additional embodiments of the present invention are related to the synthesis of various oxygenated compounds using the epoxydiol (12) described above as a synthon and as illustrated in schemes 1 and 3 herein.

DETAILED DESCRIPTION OF THE INVENTION

As used in the present invention "suitable or appropriate solvents" include but are not limited to water, water miscible solvents such as dialkylketones with 2–4 carbon atoms, lower alcohols with 1–3 carbon atoms, cyclic ethers and ethers with 2–6 carbon atoms or mixtures thereof.

As used herein "reducing agent" includes but is not limited to a transition metal reagent, a hydride reagent or trialkysilane, preferably SmI₂, tributyltinhydride or tris(trimethylsilyl)silane. These reducing agents may be used in combination with radical initiation agents such as UV light and/or AIBN or dibenzoylperoxide or a similar initiator.

As used herein "acid catalyst" includes but is not limited to mineral acids, such as HCl; organic acids such as p-toluene sulfonic acid; acid ion exchange resin such as Amberlyst 15, Amberlyst IR 118, Amberlite CG-50, Dowex 50X8-100; all commercially available from Aldrich or similar acidic ion exchange resins.

As used herein "alkaline catalyst" includes but is not limited to alkaline metal hydroxide or alkaline earth metal hydroxides, such as LiOH, NaOH, KOH, or Ba(OH)₂; carbonate or bicarbonate of alkaline metal, such as Na₂CO₃ or $K_2CO_3$; $Al_2O_3$ or basic ion exchange resin such as Amberlite IRA-400, Amberlyst A26, Amberlyst A21, Dowex 1X2-200 or other ion exchange resins.

In an embodiment of the present invention, the compound 12 can be synthesized by forming an acetonide such as compound 11 wherein X is as defined as a substituent selected from the group consisting of, but not limited to hydrogen, halogen, alkyl of 1–5 carbon atoms, aryl or CN., preferably X is Cl, Br, methyl, phenyl or CN. The acetonide 11 is then exposed (contacted) to permanganate in an appropriate solvent at an appropriate temperature to yield the epoxydiol. In a preferred embodiment of the present invention, at least about 1.5 equivalents of $KMnO_4$ are used and more preferably between about 1.5–2.5 equivalents. When less equivalents of permanganate are used and higher temperatures are used, a side product of this reaction may be formed to a larger extent. Such side product is the diol 13 shown in scheme 1.

As used in this invention, an appropriate solvent for the synthesis of compound 12 includes but is not limited to water, dialkylketones with 2–4 carbon atoms, lower alcohols with 1–3 carbon atoms, cyclic ethers such as tetrahydrofuran (THF) or dioxane and mixtures thereof. Preferred solvents are mixtures of water and acetone or water and an alcohol.

As used in this invention, an appropriate temperature range for the synthesis of compound 12 is from about −78° C. to +40° C., preferably from about −15° C. to about +10° C. It is further understood that depending on the pH range of the reaction mixture, the stability of the desired compound may be effected. Therefore, in a preferred embodiment of the present invention, and particularly a preferred method for the synthesis of compound 12 the pH of the reaction should be maintained between about 4–8.

Any known method for controlling pH can be used, for example a buffering agent or system can be used to maintain such pH range, or one could saturate the reaction mixture with $CO_2$ or buffer the reaction mixture using some organic or inorganic weak acid such as acetic or boric acid, or by using a buffer working in the region of pH from about 4–8, such as phosphate buffer, acetate buffer, tetraborate buffer or borate buffer. In a preferred process for synthesizing compound 12, magnesium sulfate ($MgSO_4$) is used to maintain the pH between about 4–8. If the reaction mixture is allowed to go above about pH 8, the desired product 12 will be made, although it may be subject to rapid decomposition.

As demonstrated in scheme 1, the exposure of acetonide 11 to 2 eq of aqueous $KMnO_4/MgSO_4$ at −10° to 5° C. gave an 8:1 mixture of diols 12 and 13 in 60% yield, while higher temperature and lower concentration of the reagent afforded the expected diol 13 as a major product. The formation of 12 is both unexpected and unusual based on: a) the precedent in the literature regarding the oxidation of simple dienes with permanganate [See: Lee, D. G. in The Oxidation of Organic Compounds by Permanganate Ion and Hexavalent Chromium, Open Court Publishing Company, (La Salle),1980. Two examples of formation of epoxydiols in low yields from permanganate oxidation of conjugated dienes not containing halogens have been reported: von Rudloff, E. *Tetrahedron Lett.* 1966, 993; and Sable, H. Z.; Anderson, T.; Tolbert, B.; Posternak, T. *Helv. Chim. Acta* 1963, 46, 1157]; b) the known instability of a-haloepoxides, [See: Carless, H. A. J.; Oak, O. Z. *J. Chem. Soc. Chem. Commun.,* 1991, 61 ;Ganey, M. V.; Padykula, R. E.; and Berchtold, G. A. *J. Org. Chem.* 1989, 54, 2787]; and c) the unavailability of data concerning direct and controlled oxidation of 1-chloro-1,3-dienes with $KMnO_4$ or $OsO_4$.

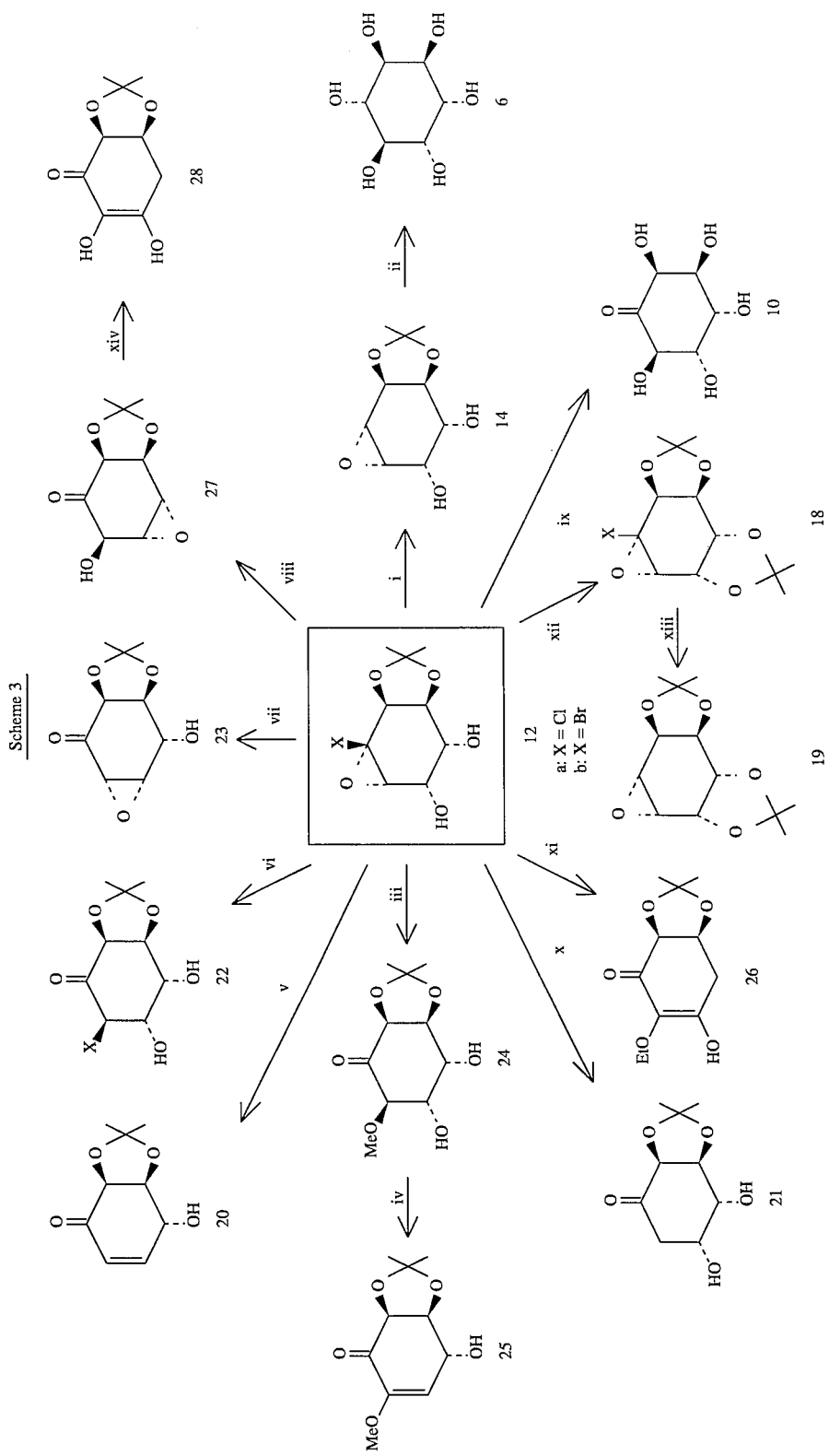

As shown in scheme 3 above, the synthon 12 can be used to make several oxygenated compounds. Although applicants have illustrated and/or exemplified a finite number of compounds which can be made using the synthon 12, as a starting material, it is understood that those skilled in the art could readily prepare additional compounds. For example, see scheme 4 below which shows the synthesis of insoitols 3,4 and 5 from the synthon 12. These additional compounds are contemplated by the present invention.

Scheme 4
Synthesis of Inositols: D-chiro-inositol 6, neo-inositol 5, mucoinositol 4 and allo-inositol 3 from the haloepoxide 12a.

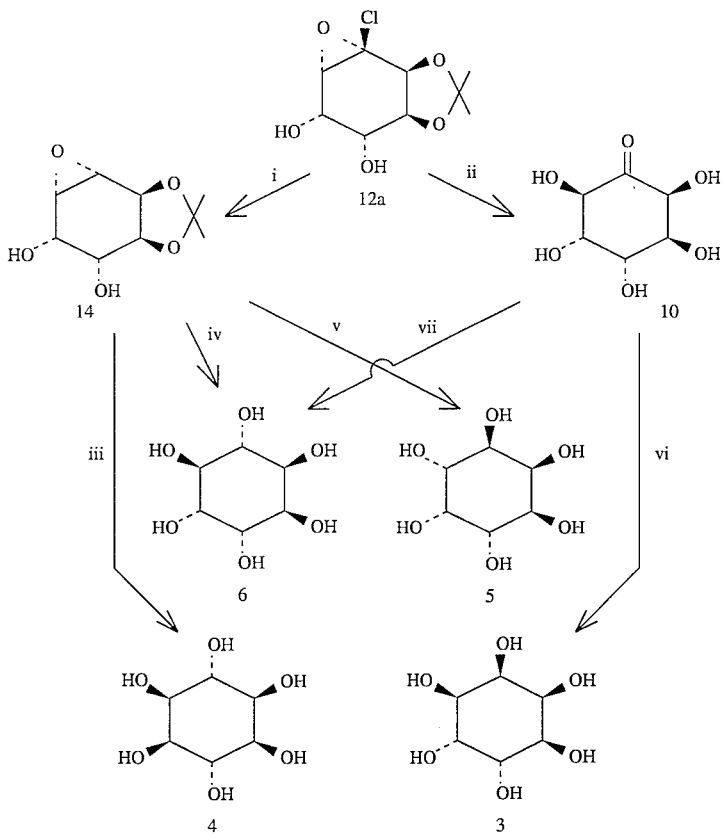

Reagents: (i) TTMSS/AlBN; (ii) Al$_2$O$_3$/H$_2$O; (iii) H$_2$O/Amberlyst 15/25° C.; (iv) H$_2$O/sodium benzoate/100° C.; (v) H$_2$O/Amberlyst IR-118/100° C.; (vi) H$_2$/RaNi/MeOH; (vii) NaBH$_4$/CH$_3$CN.

Depending on the desired product, compound 12 can be reacted with a reducing agent such as a hydride reagent or trialkysilane and preferably with tributyltinhydride or tris(trimethylsilyl)silane. This reaction, if necessary as understood by those skilled in the art, may be carried out under conditions of radical initiation such as UV light and/or in the presence of an appropriate radical initiator such as AlBN or dibenzoylperoxide or a radical initiator of a similar nature. Following reduction of the epoxide 12 as described above, the epoxide 14 can be opened and deprotected using pure water, an acid catalyzed hydrolysis with mineral acid, (HCl), an organic acid p-toluene sulfonic acid) or an acidic ion exchange resin including but not limited to Amberlyst 15, Amberlyst IR 118, Amberlite CG-50, Dowex 50 X 8-100, or an alkaline catalysed hydrolysis with weak bases such as a salt of organic acid, preferably sodium benzoate, sodium acetate or sodium citrate, or an alkaline ion exchange resin included but not limited to Amberlyst A 21 or organic bases including but not limited to aliphatic amines such as triethylamine or diisopropylamine. Reaction temperatures range from about −10° C. to about 110° C., and preferably from about 50° C. to about 90° C., in water or an appropriate solvent mixture such as water with a water miscible solvent such as lower ketones with 2–4 carbon atoms, lower alcohols with 1–3 carbon atoms, or cyclic ethers with 4 carbon atoms or ethers with 2–6 carbon atoms.

Compound 12 proved remarkably stable ($t_{1/2}$ at 110° C.=approximately 50 hr) and was transformed to the known epoxide 14 [See: Hudlicky, T.; Price, J. D.; Rulin, F.; Tsunoda, T. *J. Am. Chem. Soc.* 1990, 112, 9439; and Hudlicky, T.; Price, J. Luna, H.; Andersen, C. M. *Isr. J. Chem.* 1991, 31, 229.] upon reduction with tris(trimethylsilyl)silane/AlBN [Chatgilialoglu, C.; Griller, D.; Lesage, M. *J. Org. Chem.* 1988, 53, 3642] in 50% yield. The opening of this epoxide with H$_2$O in the presence of small amount of sodium benzoate gave, in unoptimized runs, almost pure D-chiro-inositol, identical with authentic samples ($^1$H-NMR and GC)

Scheme 5
Synthesis of D-chiro-inositol via chiro-3-inosose

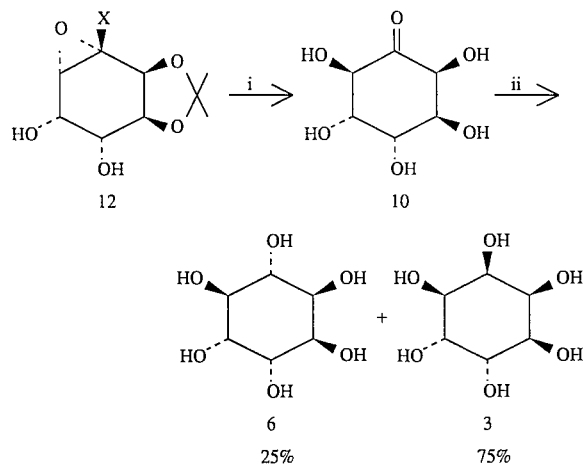

(i) H$_2$O; (ii) NaBH$_4$

Direct hydrolysis of 12 with H$_2$O in the presence of Al$_2$O$_3$ furnished almost quantitatively the rare inosose 10. This reaction can be carried out using water or using an alkaline catalysis with alkaline ion exchange resin such as Amberlite IRA-400, Amberlyst A 26, Amberlyst A 21, Dowex IX2-200 or ion exchange resin of similar nature, or Al$_2$O$_3$ or a mixture of these; or using acid catalysis by mineral acid such as HCl or organic acid such as acetic acid, or p-toluenesulfonic acid (pTSA) or an acidic ion exchange resin including but not limited to Amberlyst 15, Amberlyst IR 118, Amberlite CG-50, Dowex 50X8-100, or using SiO$_2$. Reaction temperatures range from about −10° C. to about 110° C., and preferably are from about 50° C. to 100° C., and the reaction can be carried out in water or an appropriate solvent mixture such as water with a water miscible solvent such as lower ketones with 2–4 carbon atoms, lower alcohols with 1–3 carbon atoms; or cyclic ethers with 4 carbon atoms; or ethers with 2–6 carbon atoms. The resulting inosose 10 from such direct hydrolysis and deprotection can then be reduced to 6 using reducing agent such as hydride reagents, preferably zinc borohydride or sodium borohydride, in an appropriate solvent such as water, lower alcohols with 1–3 carbon atoms, cyclic ethers with 4 carbon atoms, or ethers with 2–6 carbon atoms or a mixture thereof at a temperature of from about −10° C. to about 110° C. Reaction product of such reduction contains a significant amount of 6 (about 25%) separable by using known methods (See Loewus, F. A. *Methods in Plant Biochemistry* 1990, 2, 219; Honda, S. *Anal. Biochem* 1984, 140,1)

These results constitute remarkably short and effective synthesis of D-chiro-inositol 6: five chemical steps, all but two performed in aqueous media, with a potential of further shortening of this sequence to four steps upon optimization of the reactions involved. For example, it is comtemplated that the number of steps in this synthesis may be reduced. It is clear that an attractive industrial preparation of 6 will ensue as a result of such an optimization, as will other applications to the synthesis of functionalized cyclitols. There are nine stereoisomers for hexahydroxy cyclohexanes, some of which are important as either free hydroxyls or phosphates, in the communication at the cellular level. (Posternak, T. in The Cyclitols, Hermann, Paris, 1962.) These nine compounds and all of their derivatives can be prepared by controlled functionalization of arene cis diols which are now available through biocatalysis on a commercial scale.

Experimental:
(1S,2R,3S,4S,5R,6S)-2-Chloro-5-dihydroxy-8,8-dimethyl-2,3-oxa-7,9-dioxabicyclo[4.3.0]nonane (12a). To a stirred solution of 1-chloro-2,3-dihydroxycyclohexa-4,6-diene (20.0 g, 0.138 mol) in a mixture of dry acetone (210 ml) and 2,2-dimethoxypropane (23.8 ml, 0,194 mol), placed in a water bath, was added pTSA (0.80 g, 4.20 mmol). After 15 min a saturated solution of Na$_2$CO$_3$ (10 ml) was added and the mixture was cooled to −5° C. (solution A). KMnO$_4$ (50.0 g, 0.316 mol) and MgSO$_4$ (21.0 g, 0.175 mol) were dissolved in water (1250 ml) and cooled to 5° C. (solution B). To a mixture of ice (250 g) and acetone (300 ml) cooled to −15° C. was added 50 ml of solution B. Then solutions A and B were simultaneously added over 25 min, maintaining a small excess of KMnO$_4$ in the reaction mixture and temperature under 5° C. Precipitated MnO$_2$ was filtered off and washed with water and acetone. The resulting colorless solution was extracted with CHCl$_3$, the extract was dried and evaporated under reduced pressure to give 19.1 g of white solid containing 80% of 12a, 10% of 13 and 10% of 27. Recrystallization of the crude product from the mixture of EtOAc/hexane/Et$_2$O yielded in two crops 10.5 g (32%) of pure 12a. M.p.=113°–114.5° C.; [α]$_D^{20}$=+29.2° (c 1, CHCl$_3$); IR (CHCl$_3$) n 3392; 2983; 2914; 1374; 1220; 1167, 1045 cm$^{-1}$; $^1$H NMR (CDCl$_3$) d 4.63 (dd, J=5.9, 1.1 Hz, 1H), 4.56 (dd, J=5.8, 3.3, Hz, 1H), 4.29 (ddd, J=9.5, 4.3, 1.0 Hz, 1H), 4.07 (dddd, J=12.0, 4.3, 3.3., 1.0, 1H), 3.84 (ddd, J=1.1, 1.0, 1.0 Hz, 1H), 2.84 (bd, J=9.6 Hz, 1H), 2.41 (bd, J=12.1 Hz, 1H), 1.48 (s, 3H), 1.40 (s, 3H); $^{13}$C NMR (CHCl$_3$)d 110.4 (C), 78.5 (C), 77.1 (CH), 73.3 (CH), 67.8 (CH), 65.9 (CH), 63.7 (CH), 27.0 (CH$_3$), 24.9 (CH$_3$); MS (Cl) m/z (rel. intensity) 237 (M$_+$, 100), 221 (18), 161 (6), 143 (6): Anal. calcd for C$_9$H$_{13}$ClO$_5$: C, 45.68; H, 5.54;0 Found: C, 45.69; H, 5.49.

(1S,2R,3S,4S,5R,6S)-2-Bromo-4,5-dihydroxy-2,3-oxa-8,8-dimethyl-7,9-dioxabicyclo[4.3.0]nonane (12b). 1-Bromo-2,3-dihydroxycyclohexa-4,6-diene (4.8 g, 0.026 mol) was treated with 2,2-dimethoxypropane as described in preparation of 12a. The resulting mixture was diluted with acetone (75 ml) and cooled to 0° C. Then, maintaining the temperature under 5° C., the solution of KMnO$_4$ (6.20 g, 0.03 mol) and MgSO$_4$ (3.00 g, 0.025 mol) in a mixture of water (130 ml) and acetone (60 ml), cooled to 5° C., was added over 30 min. Precipitated MnO$_2$ was filtered off and washed with water and acetone. The filtrate was then saturated with NaCl and extracted with EtOAc. Drying and evaporation of the extract under reduced pressure yielded crude crystalline product (3.3 g), recrystallization of which (EtOAc/hexane/Et$_2$O) gave 1.63 g (22%) of pure 12b. Mother liquor was evaporated under reduced pressure and purified by flash chromatography (10% deactivated silica gel, CHCl$_3$:MeOH, 95:5) to furnish 90 mg (1.3%) of 12b, 380 mg (3.8%) of the bromo derivative 13 and 55 mg (1.1%) of 27. For 12b: IR (KBr) n 3390, 2910, 2830, 1380, 1225, 1170, 1070, 1045 cm$^{-1}$;$^1$H NMR (CDCl$_3$) d4.65 (dd, J=5.8, 1.3 Hz, 1H), 4.56 (dd, J=5.7, 3.4 Hz, 1H, 4.32 (bdd, J=10.1, 4.3 Hz, 1H), 4.11 (dm, J=12.0 Hz, 1H), 3.91 (m, 1H), 2.81 (bd, J=10.2 Hz, 1H), 2.38 (bd, J=12.1 Hz, 1H), 1.49 (s, 3H), 1.39 (s, 3H); $^{13}$C NMR (CDCl$_3$) d 110.5 (C), 77.2 (C), 74.2 (CH), 71.6 (CH), 67.9 (CH), 66.5 (CH), 63.7 (CH), 27.1 (CH3), 25.1 (CH$_3$); and For (1S,3R,4R,5R,6S)-8.8-dimethyl-3-hydroxy-4,5-oxa-2-oxo-7,9-di-oxabicyclo[4.3.0]nonane (27): M.p.=126°–127° C.; [a]$^D$20=+61.1° (c 1, CHCl$_3$); IR (KBr) n 3555, 3045, 2995, 1755, 1440, 1405, 1263, 1235, 1110, 1073 cm$^{-1}$; $^1$H NMR (CDCl$_3$) d 5.13 (dd, J=5.8, 1.4 Hz, 1H), 4.86 (ddd, J=5.9, 1.4, 1.4 Hz, 1H), 4.42 (dd, J=5.9, 1.5 Hz, 1H), 3.67 (ddd, J=3.8, 1.4, 1.4 Hz, 1H), 3.39 (ddd, J=3.8, 1.4, 1.4 Hz, 1H), 3.31 (bd, J=5.8 Hz, 1H), 1.60 (s, 3H), 1.39 (s, 3H); $^{13}$C NMR (CDCl$_3$) d 202.4 (C),113.2 (C), 78.2 (CH), 77.4 (CH), 70.0 (CH), 59.5 (CH), 54.0 (CH), 27.3 (CH$_3$), 25.3 (CH$_3$); MS (Cl) m/z (rel. intensity) 201 (M+, 100), 143 (12), 125 (14), 111 (14); Anal. calcd for C$_9$H$_{12}$O$_5$: C, 54.00; H, 6.04; Found: C, 53.83; H, 6.03.

(1S,2S,3S,4S,8R,9R )-2-Chloro-2,3-oxa-6,6,11,11-tetramethyl-3,7,10,12-tetraoxatricyclo[7.3.0.0$^{4,8}$]dodecane (18a). To a stirred solution of 12a (1.14 g, 4.82 mmol) in dichloromethane (6.0 ml) and 2,2-dimethoxypropane (1.8 ml, 14.6 mmol) was added pTSA (10 mg, 0.053 mmol). After 2.5 h was added a saturated solution of Na$_2$CO$_3$ (0.5 ml) and water (25 ml) and the reaction mixture was extracted with petroleum ether. The extract was dried and evaporated under reduced pressure to give 1.24 g (93%) of colorless crystalline 18a. M.p.=59°–62.5° C.; [a]$^D$20=+23.1° (c 1, CHCl$_3$); IR (KBr) n 2981, 2930, 1378, 1261, 1214, 1162, 1072, 1053 cm$^{-1}$; $^1$H NMR (CDCl$_3$) d 4.62 (m, 3H), 4.35 (ddd, J=6.3, 1.7, 1.0 Hz, 1H), 3.64 (ddd, J=1.8, 1.0, 1.0 Hz, 1H), 1.48+1.47 (s, 6H), 1.40 (s, 3H), 1.36 (s, 3H); $^{13}$C NMR (CDCl$_3$) d 111.0 (C), 110.6 (C), 79.0 (C), 76.2 (CH), 74.7 (CH), 74.2 (CH), 72.1 (CH), 62.2 (CH), 27.4 (CH$_3$), 26.8 (CH$_3$), 25.8 (CH$_3$), 25.3 (CH$_3$); MS (Cl) m/z (rel. intensity) 277 (M+, 63), 261 (80), 245 (10), 219 (15), 183 (40), 161 (43), 143 (72), 133 (62), 125 (45), 115 (75); Anal. calcd for C$_{12}$H$_{17}$ClO$_5$: C, 52.09; H, 6.19; Found: C, 52.24;H, 6.22.

(1R,2S,3R,4R,8S,9S )-2,3-Oxa-6,6,11,11-tetramethyl-3,7,10,12-tetraoxatricyclo[7.3.0.0$^{4,8}$]dodecane (19). A solution of 18a (60.0 mg, 0.239 mmol), tri-n-butyltinhydride (76.3 mg, 0.262 mmol) and AlBN (19.6 mg, 0.119 mmol) in benzene (1.5 ml) was heated for 2.5 h under argone to 75° C. The reaction mixture was then diluted with petroleum ether (5 ml) and filtered through 10% deactivated silica gel. Washing of the silica gel with EtOAc and evaporation of the eluent under reduced pressure yielded waxy crystalline product (75 mg), whose flash chromatography (10% deactivated silica gel, hexane:EtOAc, 7:1) furnished 19 (25 mg, 43%). M.p=109°–110° C.; IR (KBr) n 3035, 2980, 1395, 1380, 1250, 1225, 1095, 1075, 1045 cm$^{-1}$; $^1$H NMR (CDCl$_3$) d 4.57 (m, 3H), 4.34 (bd, J=6.5 Hz, 1H), 3.34 (m, 2H). 1.52 (s, 3H) 1.41 (s, 3H), 1.37 (s, 6H); $^{13}$C NMR (CDCl$_3$) d 109.3 (C), 108.9 (C), 74.5 (CH), 72.5 (CH), 71.5 (CH), 69.9 (CH), 55.1 (CH), 52.3 (CH), 27.4 (CH$_3$), 26.5 (CH$_3$), 25.8 (CH$_3$), 25.0 (CH$_3$); MS (Cl) m/z (rel. intensity) 243 (M+, 37), 227 (50), 185 (100), 169 (10), 127 (40); Anal calc. for C$_{12}$H$_{18}$O$_9$: C, 59.49: H, 7.49; Found: C, 59.58: H, 7.52.

Reduction of haloepoxides 12a,b with tris(trimethylsilyl)silane

A) A solution of 12b (112 mg, 0.398 mmol), tris(trimethylsilyl)silane (147 mg, 0.477 mmol) and AlBN (25 mg, 0.152 mmol)in toluene (2 ml) was heated under argon for 1.5 h to 110° C. Then the reaction mixture was evaporated under reduced pressure to dryness and the residue was flash chromatographed (10% deact. silica gel, CHCl$_3$:MeOH, 95:5) to furnish 38.4 mg (48%) of crystalline 14 and 3.9 mg (5%) of 21. B) The solution of 12a (130 mg, 0.522 mmol) and AlBN (25 mg, 0.152 mmol) in toluene (1.5 ml) was heated for 6 h under argon to 105° C. Flash chromatography (10% deact. silica gel, CHCl$_3$;MeOH, 95:5) of under reduced pressure evaporated reaction mixture yielded 37.1 mg (42%) of 14 and 16.2 mg (13%) of 22. For (1S,3R,4S,5R,6S)-3-chloro-4,5-dihydroxy-8,8-dimethyl-2-oxo-7,9-dioxa[4.3.0]nonane (14): M.p.:105°–108° C.; [a]$_D$$^{20}$=110.5° (c 1, CHCl$_3$), IR (KBr) n 3600–3100, 3030, 2955, 1755, 1385, 1245, 1170, 1085 cm$^{-1}$;1H NMR (CDCl$_3$) d 4.93 (dd, J=10.7, 0.7 Hz, 1H), 4.63 (d, J=5.2 Hz, 1H), 4.56 (dd, J=2.9, 2.6 Hz, 1H), 4.53 (dd, J=5.2, 2.9 Hz, 1H), 3.97 (dd, J=10.7, 2.6 Hz, 1H), 2.93 (bs, 2H), 1.41+1.40 (s, 6H); $^{13}$C NMR (CDCl$_3$) d 201.7 (C), 117.3 (C), 86.8 (CH), 74.9 (CH), 70.8 (CH), 66.3 (CH), 27.6 (CH$_3$), 26.2 (CH$_3$).

Reduction of 12a with SmI$_2$

A) To a solution of 12a (52.1 mg, 0.220 mmol)in a mixture of THF (1 ml) and MeOH (0.3 ml) under argon, was added dropwise over the period of 30 min at −90° C. a solution of SmI$_2$ (0.1M in THF, 2.5 ml, 0.230 mmol). After 1 h of stirring without cooling a saturated solution of K$_2$CO$_3$ (1 ml) was added and the reaction mixture was stirred for an additional 15 min. Extraction with EtOAc, drying and evaporation of the extract under reduced pressure gave the crude solid product. Flash chromatography (10% deact. silica gel. CHCl$_3$:MeOH, 95:5, then 9:1) furnished 7.2 mg (18%) of 20 and 22 mg (49%) of 21. For (1S,4R,5R,6S)-3,4-dihydroxy-8,8-dimethyl-2-oxo-7,9-dioxabicyclo[4.3.0] nonane (21): IR (KBr) n 3450, 3060, 2970, 1750, 1155, 1100 cm$^{-1}$ ; $^1$H NMR (CDCl$_3$) d 4.45 (dd. J=6.3, 3.6 Hz, 1H), 4.49 (bd, 6.5 Hz, 1H), 4,29 (m, 1H), 4.17 (m, 1H), 2.81 (ddd, J=15.0, 8.2, 1.0 Hz, 1H), 2.67 (dd, 15.0, 5.3 Hz, 1H), 2.51 (bd, J=3.3 Hz, 1H), 2.22 (bd, J=4.6 Hz, 1H), 1.44 (s, 3H), 1.41 (s, 3H); $^{13}$C NMR (CDCl$_3$) d 206.7 (C), 110.5 (C), 78.2 (CH), 77.0 (CH), 70.8 (CH), 68.1 (CH), 42.6 (CH$_2$), 26.7 (CH$_3$), 25.1(CH$_3$); MS (Cl) m/z (rel. intensity) 203 (M+, 70), 187 (35), 159 (15), 145 (30), 127 (100); Anal. calcd for C$_9$H$_{14}$O$_5$: C,53.46; H, 6,98; Found: C, 53.25; H. 6.93. B) Analogous treatment of 12a (420 mg, 1.78 mmol) with solution of SmI$_2$ (0.1M in THF, 18.0 ml, 1.95 mmol) added over the period of 2 min yielded after chromatography (10% deact. silica gel, CHCl$_3$:MeOH, 95:5) 77 mg (22%) of 21 and a complex mixture of products (190 mg). Chromatography (10% deact. silica gel. EtOAc:hexane, 1:1) of this mixture furnished 110 mg (31%) of 23. For (1S,3S,4S,5R)-8,8-dimethyl-5-hydroxy-3,4-oxa-2-oxo-7,9-dioxabicyclo [4.3.0]nonane (23): [a]$_D$$^{20}$=−84.8° (c 1.6, CHCl$_3$); IR (KBr) n 3590, 3060, 3030, 2980, 1760, 1405, 1240, 1185, 1100, 895 cm$^{-1}$; $^1$H NMR (CDCl$_3$) d 4.75 (bd, J=9.1, 1H). 4.53 (dd, J=9.1, 6.6 Hz, 1H), 4.10 (dd, 6.5, 4.3 Hz, 1H), 3.70 (d, J=4.6 Hz, 1H), 3.61 (d, J=4.4 Hz, 1H), 2.75 (m, 1H), 1.49 (s, 3H), 1.37 (s, 3H); $^{13}$C NMR (CDCl$_3$) d 201.1 (C), 109.8 (C), 78.0 (CH), 76.0 (CH), 71.5 (CH), 58.6 (CH), 54.9 (CH), 26.3 (CH$_3$), 23.9 (CH$_3$); MS (Cl) m/z (rel. intensity) 201 (M+, 100), 185 (20), 143 (15), 125 (15).

(1S,3R,4S,5R,6S)-4,5-Dihydroxy-8,8-dimethyl-3-methoxy-2-oxo-7,9-dioxabicyclo[4.3.0]nonane (24). A mixture of 12a (141 mg, 0.596 mmol), Zn powder (100 mg) and MeOH (5 ml) was refluxed under argon for 1.5 h. The solid was filtered off and washed with EtOAc. After the addition of Na$_2$CO$_3$ (0.5 ml of saturated solution) and water, the filtrate was extracted with EtOAc. Evaporation and drying of the extract under the reduced pressure furnished 110 mg of crude product. Flash chromatography (10% deactivated silica gel, CHCl$_3$: MeOH, 95:5) furnished 77 mg (56%) of 24, 27 mg (21%) of 25 and 8 mg (6%) of staring material 12a. For (1S,3R,4S,5R,6S)-4,5-dihydroxy-8,8-dimethyl-3-methoxy-2-oxo-7,9-dioxabicyclo[4.3.0]nonane (24): IR (CHCl$_3$) n 3457, 2989, 2936, 1742, 1384, 1226, 1158, 1078 cm$^{-1}$; $^1$H NMR (CDCl$_3$) d 4.59 (bd, J=4.9 Hz, 1H), 4.51 (m, 2H), 4.19 (bd, J=10.4 Hz, 1H), 3.93 (bd, J=10.3 Hz, 1H), 3.56 (s, 3H), 2.92 (bs, 2H), 1.39 (s, 6H); $^{13}$C NMR (CD$_3$OD) d 207.8 (C), 129.3 (CH), 111.6 (C), 85.1 (CH), 79.5 (CH), 73.2 (CH), 69.7 (CH), 59.7 (CH$_3$), 27.4 (CH$_3$), 26.1 (CH$_3$); MS (Cl) m/z (rel. intensity) 233 (M+, 12), 215 (15), 201 (12), 183 (63), 174 (25), 157 (70), 143 (90), 125 (100); Anal. calcd for C$_{10}$H$_{16}$O$_6$: C, 51.72; H, 6.94; Found: C, 51.64; H, 6.98.

For (1S,5R,6S)-8,8-dimethyl-5-hydroxy-3-methoxy-2-oxo-7,9-dioxabicyc-lo[4.3.0]non-3-ene (25): IR n (CHCl$_3$) 3520, 3050, 2995, 1720, 1655, 1395, 1245, 1180, 1160, 1095 cm$^{-1}$; $^1$H NMR (CDCl$_3$) d 5.80 (dd, J=5.4, 1.2 Hz, 1H), 4.79 (ddd, J=5.5, 5.0, 3.0 Hz, 1H), 4.59 (d, J=5.5 Hz, 1H), 4.51 (ddd, J=5.3, 3.0, 1.2 Hz, 1H); 3.69 (s, 3H), 2.22 (bs, J=5.0 Hz, 2H), 1.42 (s, 3H), 1.39 (s, 3H); $^{13}$C NMR (CD$_3$OD) d 192.4 (C), 151.9 (C), 115.5 (CH), 111.2 (C), 80.0 (CH), 76.6 (CH), 65.0 (CH), 55.8 (CH$_3$), 27.0 (CH$_3$), 26.0 (CH$_3$); MS (Cl) m/z (rel. intensity) 215 (M+, 10), 197 (75), 169 (20), 157 (100), 139 (100), 127 (100); Anal. calcd for $C_{10}H_{14}O_5$: C, 56.07; H, 6.59: Found: C, 55.95; H, 6.63.

(1S,6S)-8,8-Dimethyl-3-ethoxy-4-hydroxy-2-oxo-7,9-dioxabicyclo[4.3.0]-non-3-ene (26). A mixture of 12a (375 mg, 1.59 mmol), benzylamine (340 mg, 3.17 mmol) and THF (2 ml) was stirred at −25° C. for 10 h. Then acetone (6 ml) was added and precipitated benzylamine hydrochloride was filtered off at −25° C. To the filtrate at −20° C. was added oxalic acid (142 mg, 1.59 mmol) and after 10 min the mixture was filtered to give 430 mg of white solid. This solid (188 mg) was then heated to reflux in ethanol (5 ml). Precipitated benzylamine oxalate was filtered off and evaporation of the filtrate under reduced pressure yielded 110 mg of the crude product. By flash chromatography (10% deactivated silica gel, $CHCl_3$:MeOH, 95:5) was obtained 46.8 mg (26%) of 26 and 16 mg of 28 were obtained. For 26: M.p.=107°–110° C. (dec); $[a]_D^{20}$=+102° (c 0.5, MeOH); IR ($CHCl_3$) n 3450, 3050, 3035, 1670, 1650, 1400, 1320, 1275, 1230, 1140, 1115, 1045 $cm^{-1}$; $^1H$ NMR ($CDCl_3$) d 5.51 (bs, 1H) 4.89 (d, J=8.4 Hz, 1H), 3.83 (ddd, J=11.4, 8.4, 5.2 Hz, 1H), 3.75 (dq, J=9.2, 7.1 Hz, 1H), 3.64 (dq, J=9.3, 7.1 Hz, 1H), 2.93 (ABq, J=16.8, 5.2 Hz, 1H), 2.41 (ABq, J=16.8, 11.5 Hz, 1H), 1.69 (s, 3H), 1.60 (s, 3H), 1.24 (t, J=7.0 Hz, 3H); $^{13}C$ NMR ($CDCl_3$) d 189.9 (C), 148.0 (C), 126.3 (C), 117.9 (C), 80.3 (CH), 77.1 (CH), 65.6 ($CH_2$), 39.2 ($CH_2$), 26.6 ($CH_3$), 24.3 ($CH_3$), 15.3 ($CH_3$); MS (Cl) m/z (rel. intensity) 229 (M+, 100), 183 (30), 170 (20), 143 (25), 127 (10); Anal. calcd for $C_{11}H_{16}O_5$: C, 57.89; H, 7.07; Found: C, 57.98; H, 6.98.

(1S,6S)-8,8-Dimethyl-3,4-dihydroxy-2-oxo-7,9-dioxabicyclo[4.3.0]non-3-ene (28). A mixture of 27 (0.23 g), 10% deactivated silica gel (5 g, Silica Gel 60, EM Science), ethylacetate (12 ml) and hexane (8 ml) was stirred at room temperature for 2 h. The mixture was then filtered and the filtrate was evaporated under reduced pressure. Flash chromatography (10% deact. silica gel, ethylacetate:hexane, 6:4) furnished 25 mg (11%) of 28. M.p.=153°–154° C.; $[a]_D^{20}$= +102° (c 0.5, MeOH); IR (KBr) n 3295, 2465, 1635, 1410, 1335, 1175, 1140 $cm^{-1}$; $^1H$ NMR ($CDCl_3$) d 5.45 (bs, 1H), 4.85 (d, J=8.3 Hz, 1H), 4.18 (m, 1H), 2.88 (d, J=16.7, 5.4 Hz, 1H), 2.49 (dd, J=16.8, 11.6 Hz, 1H), 2.43 (bs, 1H), 1.69 (s, 3H), 1.61 (s, 3H); $^{13}C$ NMR ($CD_3OD$) d 192.5 (C), 151.9 (C), 128.2 (C), 120.0 (C), 86.1 (CH), 82.2 (CH), 43.4 ($CH_2$), 26.9 ($CH_3$), 24.4 ($CH_3$); MS (Cl) m/z (rel. intensity) 201 (M+,100), 85 (23), 81 (15), 69 (23).

D-chiro-inositol (6) A) A mixture of 14 (16.2 mg, 0.080 mmol), ion exchange resin Amberlyst 15 (100 mg) and water (1.5 ml) was heated for 3.5 h to 80° C. Filtering off the resin, washing with water and evaporation of the filtrate under reduced pressure yielded 12 mg of crystalline product containing 70% of 6 (based on $^1H$ NMR). B) A mixture of 14 (9.7 g, 44.05 mmol), sodium benzoate (30 mg, 0. 21 mmol) and water (150 ml) was refluxed in darkness, under argon for 83 h. The reaction mixture was evaporated, dissolved in a mixture of water and methanol and the mixture was filtered with charcoal. The obtained colorless solution was evaporated to dryness. Recrystallization from the mixture of water and ethanol furnished 6.13 g (77%) of pure 6, identical with the natural product. C) The mixture of 10 (97 mg, 0.545 mmol), $NaBH_4$ (50 mg, 1.32 mmol) and acetonitrile (5 ml) was stirred at room temperature for 2 h. Then diluted HCl (1:1, 0.2 ml) was added, After an additional 1 h of stirring the reaction mixture was evaporated to dryness to give 180 mg of the product containing 15% of 6 ($^1H$ NMR, GC).

D-Chiro-3-inosose (10). A mixture of 12a (93.7 mg, 0.396 mmol), $Al_2O_3$ (activated, basic, Brockmann I, 150 mg) and 2 ml of water was heated while stirring for 0.5 h to 80° C. After filtering off the $Al_2O_3$, washing it and evaporation of the filtrate under reduced pressure, 72 mg (84%) of 10 was obtained. IR (KBr) n 3346, 3006, 1735, 1576, 1420, 1302, 1132, 1078, 1005 $cm^{-1}$; $^1H$ NMR ($D_2O$) d 4.40 (dd, J=3.4, 1.3 Hz, 1H), 4.16 (dd, J=9.7, 1.3 Hz, 1H), 3.94 (dd, J=4.1, 3.0 Hz, 1H), 3.84 (dd, J=4.1, 3.2 Hz, 1H), 3.59 (dd, J=9.7, 3.1 Hz, 1H); $^{13}C$ NMR ($D_2O$) d 208.0 (C), 75,7 (CH), 74.1 (CH), 73.6 (CH), 73.3 (CH), 71.1 (CH).

Neo-inositol (5). A mixture of epoxide 14 (0.69 g, 3.41 mmol), Amberlyst IR-118 (1.5 g) and water (10 ml) was stirred when heated to about 100° C. for 30 min. The solid was filtered off, the solution was filtered with charcoal and evaporated to give 0.54 g (87%) of the mixture containing 70% of 6 and 25% of 5. Recrystallization of this product from aqueous ethanol furnished 96 mg of 5.

Muco-inositol (4). A mixture of epoxide 14 (0.58 g, 2.86 mmol), Amberlyst 15 (0.66 g) and water (20 ml) was stirred at room temperature for 24 h. The solid was filtered off, the solution was filtered with charcoal and evaporated to give 0.43 g (83%) of colorless product containing >90% of 4. Recrystallization of the crude product from aqueous ethanol furnished 4 (0.34 g) of >95% purity.

Allo-inositol (3). A mixture of inosose 10 (1.15 g, 6.45 mmol), Raney nickel (0.5 g) and methanol (15 ml) was hydrogenated at 60 psi for 24 h. The reaction mixture was then diluted with water, filtered with charcoal and evaporated to dryness to furnish 0.91 g (78%) of the crude yellow product containing >90% of 3. Recrystallization of this product (0.626 g) from aqueous ethanol gave 0.24 g of 3.

What is claimed is:

1. A process for the preparation of D-chiro-3-inosose 10,

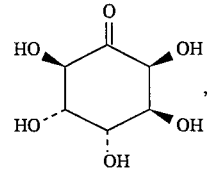

the process comprising reacting an epoxydiol having the formula:

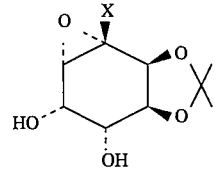

wherein X is Cl or Br;

with an appropriate hydrolyzing agent at a temperature between about −10° C. to about 110° C. in an appropriate solvent.

2. A process of claim 1 wherein the hydrolyzing agent is selected from the group consisting of water, an alkaline or acidic catalyst, $Al_2O_3$ or an alkaline or acidic ion exchange resin.

3. A process of claim 2 wherein the hydrolyzing agent is $Al_2O_3$.

4. A process of claim 1 wherein the temperature is between about 50° C. to about 100° C.

5. A process of claim 1 wherein the solvent is water, a water miscible solvent or a mixture thereof.

* * * * *